United States Patent [19]

Matsuda

[11] 4,056,565

[45] Nov. 1, 1977

[54] PROCESS FOR THE PRODUCTION OF ACRYLAMIDE AND METHACRYLAMIDE

[75] Inventor: Fujio Matsuda, Fujisawa, Japan

[73] Assignee: Mitsui Toatsu Chemicals, Incorporated, Tokyo, Japan

[21] Appl. No.: 56,967

[22] Filed: July 21, 1970

[30] Foreign Application Priority Data

July 24, 1969 Japan .................................. 44-58021
Oct. 9, 1969 Japan .................................. 44-80309
Nov. 4, 1969 Japan .................................. 44-87593
Nov. 25, 1969 Japan .................................. 44-93945

[51] Int. Cl.$^2$ ........................................ C07C 103/133
[52] U.S. Cl. ............................................... 260/561 N
[58] Field of Search ...................... 260/561 R, 561 N

[56] References Cited

U.S. PATENT DOCUMENTS 3,597,481  8/1971  Tefertiller et al. ................... 260/561
3,631,104  12/1971  Habermann et al. ............ 260/561 N
3,642,894  12/1972  Habermann et al. ............ 260/561 N
3,670,021  6/1972  Goetz et al. ...................... 260/561 R

FOREIGN PATENT DOCUMENTS 551,869  6/1932  Germany ......................... 260/561 R

OTHER PUBLICATIONS

Watanabe, Bulletin Chem. Soc. Japan, Sept. 1964, pp. 1325-1329.

Primary Examiner—Ethel G. Love
Attorney, Agent, or Firm—Eugene Sabol

[57] ABSTRACT

Process for the production of acrylamide or methacrylamide wherein acrylonitrile or methacrylonitrile is reacted with water and/or water donor in the presence of a catalyst consisting essentially of Raney copper, Ullman copper, reduced copper catalyst, copper with a carrier, silver, gold, cobalt, palladium and/or platinum.

5 Claims, No Drawings

PROCESS FOR THE PRODUCTION OF ACRYLAMIDE AND METHACRYLAMIDE

This invention relates to a process for the production of acrylamide or methacrylamide wherein acrylonitrile or methacrylonitrile is hydrated. More particularly, this invention relates to a process for the production of acrylamide or methacrylamide wherein acrylonitrile or methacrylonitrile is reacted with water and/or water donor in the presence of a catalyst.

In recent years, acrylamide and methacrylamide have been much in demand for paper reinforcing agents, soil solidifying agents, fiber treating agents, etc. and have become important chemicals. As the production of these compounds on a commercial scale was expensive, however, an economical process for the production of these compounds has been sought.

The object of the present invention is to provide a new process for the production of acrylamide and methacrylamide. It has now been found that acrylonitrile or methacrylonitrile is reacted with water or a water donor in the presence of a catalyst containing Raney copper, Ullman copper, reduced copper catalyst, copper with a carrier, silver, gold, cobalt, palladium and/or platinum, whereupon acrylamide or methacrylamide is produced.

At present, a process for the production of acrylamide or methacrylamide on an industrial scale comprises first reacting acrylonitrile or methacrylonitrile with sulfuric acid to form acrylamide sulfate or methacrylamide sulfate and successively neutralizing the sulfate to separate acrylamide or methacrylamide. According to this process, however, polymerization tends to take place during the production of acrylamide sulfate or methacrylamide sulfate and separation of acrylamide or methacrylamide by successively neutralizing said sulfate is extremely difficult.

According to the present invention, acrylamide or methacrylamide can easily be produced economically by hydrating acrylonitrile or methacrylonitrile without using sulfuric acid.

The reaction according to this invention is considered to take place, for example, as shown below.

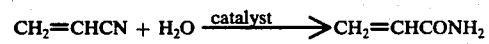

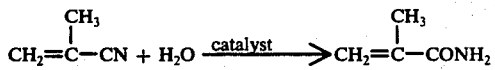

In this invention, it is most preferable to react acrylonitrile or methacrylonitrile with water. However, acrylamide or methacrylamide can be produced by employing acrylonitrile or methacrylonitrile and a water donor such as an alcohol, water-containing substance or a mixture of hydrogen and oxygen. Water donors utilizable for this invention include aliphatic monohydric alcohols such as methanol, ethanol, n-propanol, isopropanol, sec-butanol, tert-butanol, pentanol-2, pentanol-3, 2-methylbutanol-3,4-methylpentanol-2, hexanol-2, hexanol-3, etc.; aliphatic dihydric alcohols such as hexylene glycol, butylene glycol, propylene glycol, ethylene glycol, etc.; alicyclic alcohols such as cyclohexanol, etc.; water-containing solvents; and a mixture of hydrogen and oxygen or of hydrogen and air.

In this invention, no special limitation is needed for the quantity of water or a water donor used to react with acrylonitrile or methacrylonitrile. Although acrylonitrile or methacrylonitrile reacts with even a very slight amount of water or water donor, the quantity of acrylamide or methacrylamide produced from the starting acrylonitrile or methacrylonitrile becomes larger as the quantity of water or water donor becomes larger and is used in excess. Consequently, the quantity of water or water donor used is preferably 0.01–100 mol per mole of acrylonitrile or methacrylonitrile.

Utilizable as catalysts in this invention are those containing Raney copper, Ullman copper, reduced copper catalyst, copper with a carrier, silver, gold, cobalt, palladium and/or platinum.

Utilizable are said copper-containing catalysts which further contain metals such as nickel, chromium, manganese, zinc and molybdenum. When said copper-containing catalyst is used in the reaction, the copper is not substantially ionized in the reaction mixture.

The utilizable silver-containing catalysts include, for example, reduced silver, powdery silver, spongy silver and silver with a carrier. Also utilizable are silver-containing catalysts which further contain metals such as copper, nickel, chromium and zinc.

The utilizable gold-containing catalysts include, for example, reduced gold, gold oxide, powdery gold and gold with a carrier. Also utilizable are gold-containing catalysts which further contain metals such as silver, copper, nickel, chromium and zinc.

The utilizable cobalt-containing catalysts include, for example, Raney cobalt, reduced cobalt, cobalt with a carrier and Urushibara cobalt. The cobalt-containing catalysts which further contain other metals, are also utilizable.

The utilizable palladium-containing catalysts include, for example, palladium black, colloidal palladium and palladium with a carrier. The palladium-containing catalysts which further contain other metals, are also utilizable.

The utilizable platinum-containing catalysts include, for example, platinum black, colloidal platinum, platinum skeleton catalyst and platinum with a carrier. The platinum catalysts which further contain other metals are also utilizable.

The reaction proceeds even in the event the amount of said catalyst used in this invention is very slight. For example, addition of said catalyst in an amount of 0.01 g. per mol of acrylonitrile or methacrylonitrile is sufficient to make the reaction proceed. The more the amount of catalyst used, the faster the reaction proceeds, thus permitting increase of the amount of acrylamide or methacrylamide produced. Consequently, the amount of said catalyst is perferably 0.01–100 g. per mol of acrylonitrile or methacrylonitrile.

The reaction according to this invention can be carried out by employing said catalyst as suspended bed and/or fixed bed.

When this invention is carried out using a suspended bed, two or more reactors are connected in series and the reaction liquid and the catalyst are countercurrently moved to effect reaction. In this case, the phrase "the reaction liquid and the catalyst are countercurrently moved to effect reaction" is illustrated by the following operation: In the case of connecting "n" number of reactors in series, acrylonitrile or methacrylonitrile and water or water donor are supplied to the first reactor, i.e. the reactor No. 1 and the reaction liquid discharged from the reactor No. 1 is then fed into the reactor No. 2. In such manner, the reaction liquid discharged from the reactor No. 2 is fed in consecutive order into the reactor No. "n". On the other hand, the catalyst is supplied to the reactor No. "n" where the reaction is carried out in such state that the catalyst is suspended in the reaction liquid, while the catalyst discharged from the reactor No. "n" is fed into the reactor No. "n-1" where the reaction is carried out in the suspended state. Thus, the catalyst discharged from the reactor No. "n-1" is fed in regular sequence into the reactor No. 1 to effect the reaction in the suspended state.

The reaction according to this invention is carried out at room temperature (25° C.) or a temperature lower than room temperature. However, the reaction rate can be increased by elevating the reaction temperature. If the reaction temperature is raised too high, side reactions including polymerization of acrylonitrile or methacrylonitrile will tend to take place. Addition of a polymerization inhibitor such as hydroquinone is effective to inhibit such side reactions. Even if the reaction temperature is raised to 200° C. or higher, acrylamide or methacrylamide will be formed according to said reaction, but the optimum temperature is within the range of 25°–200° C.

The reaction according to this invention proceeds easily under atmospheric pressure not only in the air but also in a nitrogen, oxygen, carbon dioxide, hydrogen or the like atmosphere. It is also possible to perform said reaction under superatmospheric pressure. The reaction is not considerably affected by pressure but can be carried out under a pressure of 0–300 kg/cm$^2$. The reaction according to this invention can be carried out in either liquid phase or vapor phase.

In carrying out this invention, an organic solvent may be added to the reaction system. Solvents utilizable for this invention include methanol, ethanol, isopropanol, acetone, dimethyformamide, dimethylsulfoxide, formamide, acetamide, etc. Addition of such solvent to the reaction system permits, for example, an increase of the concentration of acrylonitrile or methacrylonitrile in water. Acrylamide or methacrylamide can previously be added as solvent to the reaction system to similarly increase the concentration of acrylonitrile or methacrylonitrile.

The following advantages can be achieved by practicing this invention: First, in the known process using sulfuric acid for preparing acrylamide or methacrylamide from acrylonitrile or methacrylonitrile wherein polymerization takes place with violet evolution of heat, removal of heat and addition of a polymerization inhibitor are needed. In the process of this invention, however, such violent evolution of heat and polymerization are virtually absent and the formation of by-products from acrylonitrile or methacrylonitrile is slight, thus making it possible to produce acrylamide or methacrylamide in an extremely high yield. Secondly, the process used in this invention for production of acrylamide or methacrylamide has a fewer number of processing steps and permits easy isolation of acrylamide or methacrylamide as product. The known process employing sulfuric acid must include neutralization of the resulting acrylamide sulfate or methacrylamide sulfate and separation of the sulfate formed by neutralization to obtain acrylamide or methacrylamide. However, the treatment for such neutralization and separation is extremely difficult in operation and greatly affects the economy of the production process. The process of this invention necessitates no neutralization and makes it easy to isolate the resulting acrylamide and methacrylamide. Thirdly, the quality of the product obtained according to the process of this invention is excellent. In the known process wherein sulfuric acid, polymerization inhibitor, neutralizing agent, etc. are used, it is very difficult to isolate acrylamide or methacrylamide in pure form.

This invention will be illustrated more in detail by the following Examples:

EXAMPLE 1

In a 100 ml. 4-necked flask were placed about 1 g. of Raney copper (Kawaken Fine Chemical, CDT-60) which had been developed and washed with water and then with isopropanol, 30.0 g. of acrylonitrile and 13.3 g. of isopropanol. Under atmospheric pressure, the mixture was refluxed with stirring for 2 hours at a reaction temperature of about 70° C.

After completion of the reaction, the catalyst was filtered off and the filtrate was evaporated to obtain about 1.5 g. of a white crystalline product. The product was dissolved into a mixture of diethyl ether and ethanol and recrystallized therefrom to yield a white crystalline product having a melting point of 84.5°–85° C. This product was identified as acrylamide, as the result of gas chromatographic analysis, elementary analysis, IR analysis and NMR analysis. Very small amounts of acetone and an indeterminable substance were also obtained as by-products.

EXAMPLE 2

In the procedure described in Example 1, 1 g. of Raney copper which had been developed and washed with water was further washed with ethanol and the composition of the reaction liquid was 30.0 g. of acrylonitrile and 10.0 g. of ethanol. The liquid was reluxed for 2 hours at a reaction temperature of about 68° C.

After completion of the reaction, the results of a gas chromatographic analysis showed that 1.2 g. of acrylamide were obtained as the product. A small amount of an indeterminable substance was also obtained as by-product.

EXAMPLE 3

In the procedure described in Example 1, about 2 g. of Raney copper which had been developed and washed with water were subjected together with a liquid mixture of 25.0 g. of water (separated into two layers) to reflux for 2 hours at a reaction temperature of about 70° C.

After completion of the reaction, the results of gas chromatographic analysis showed that 8.1 g. of acrylamide were obtained as the product. No by-product was found besides the product.

EXAMPLE 4

In the procedure described in Example 1, about 2 g. of Raney copper which had been developed and washed with water were used and a reaction liquid composed of 26.5 g. of acrylonitrile, 18.0 g. of water and 20.0 g. of dimethylformamide was refluxed for 2 hours at a reaction temperature of about 74° C.

After completion of the reaction, the results of gas chromatographic analysis showed that 6.7 g. of acrylamide were obtained as the product. Substantially no by-products were found besides the product.

EXAMPLE 5

In the procedure described in Example 1, about 2 g. of Raney copper which had been developed and washed with water were used and a reaction liquid composed of 26.5 g. of acrylonitrile, 18.0 g. of water and 15.0 g. of isopropanol was refluxed for 2 hours at a reaction temperature of about 70° C.

After completion of the reaction, the results of gas chromatographic analysis showed that 4.7 g. of acrylamide were obtained as the product. Substantially no by-products were found besides the product.

EXAMPLE 6

In the procedure described in Example 1, about 2 g. of Ullmann copper which had been prepared by treating an aqueous solution of cupric nitrate with metallic zinc were used and a liquid mixture of 25.0 g. of acrylonitrile and 25.0 g. of water (separated into two layers) was used as reaction liquid and refluxed for 2 hours at a reaction temperature of about 70° C.

After completion of reaction, the results of gas chromatographic analysis showed that 2.3 g. of acrylamide were obtained as the product. Substantially no by-products were found besides the product.

EXAMPLE 7

In the procedure described in Example 1, a reduced copper catalyst was used in place of Raney copper. 125 grams of cupric nitrate $Cu(NO_3)_2.3H_2O$ were dissolved into 1500 ml. of water and the solution was warmed to 80° C. A 20% aqueous solution of caustic potash was added dropwise to the above solution until the pH became 9-10 to obtain cupric hydroxide. The resultant cupric hydroxide was washed well with warm water until the washed solution became neutral and then dried at 100° C. 10 grams of the resulting cupric hydroxide were charged into a 100 ml. 4-necked flask and reduced for 2 hours at 170° C. with hydrogen at a flow rate of 300 ml./min. to prepare said catalyst. Into the flask containing said reduced copper catalyst was poured a liquid mixture of 25.0 g. of acrylonitrile and 25.0 g. of water and the mixture was refluxed for 2 hours at a reaction temperature of about 70° C.

After completion of the reaction, the results of gas chromatographic analysis showed that 4.2 g. of acrylamide were obtained as the product. Substantially no by-products were found besides the product.

EXAMPLE 8

In the procedure described in Example 1, a copper asbestos catalyst was used in place of Raney copper. 15 cubic centimeters of an aqueous solution of cupric nitrate (4.2 g. as copper) were absorbed on 3 g. of asbestos which had been boiled with nitric acid, washed with water and then dried. The asbestos thus treated was added in portions to 50 cc of a boiling aqueous solution of caustic soda, filtered, washed with water and then dried. The asbestos was then charged into a 100 ml. 4-necked flask and reduced for 2 hours at 260° C. with hydrogen at a flow rate of 50 ml./min. to prepare said copper asbestos catalyst. Into the flask containing the copper asbestos catalyst was poured a liquid mixture of 25.0 g. of acrylonitrile and 25.0 g. of water and the mixture was refluxed for 2 hours at a reaction temperature of about 70° C.

After completion of the reaction, the results of gas chromatographic analysis showed that 3.6 g. of acrylamide were obtained as the product. Substantially no by-products were found besides the product.

EXAMPLE 9

In the procedure described in Example 1, a copper-cyromium catalyst was used in place of Raney copper. 10 grams of copper-chromium oxide powders containing a small amount of manganese oxide (Nikki Kagaku, Copper-chromium catalyst N203) were charged into a 100 ml. 4-necked flask, reduced for 5 hours at 200 ° C. with hydrogen at a flow rate of 150 ml./min. and then cooled to room temperature while allowing introduction of a hydrogen stream. Into the flask containing the reduced copper-chromium catalyst was poured a liquid mixture of 25.0 g. of acrylonitrile and 25.0 g. of water and the mixture was refluxed for 2 hours at a reaction temperature of about 70° C.

After completion of the reaction, the results of gas chromatographic analysis showed that 2.6 g. of acrylamide and a very small amount of propionitrile were obtained as the products. Substantially no by-products were found besides the products.

EXAMPLE 10

In the procedure described in Example 1, a copper-zinc catalyst was used in place of Raney copper. 10 grams of a cylindrically shaped material comprising copper oxide and zinc oxide (Nikki Kagaku, Copper-zinc catalyst N211) were crushed to a powder, charged into a 100 ml. 4-necked flask, reduced for 2 hours at 300° C. with hydrogen at a flow rate of 100 ml./min. and then cooled to room temperature while allowing introduction of a hydrogen stream. Into the flask containing the copperzinc catalyst was poured a liquid mixture of 25.0 g. of acrylonitrile and 25.0 g. of water and the mixture was refluxed for 2 hours at a reaction temperature of about 70° C.

After completion of the reaction, the results of gas chromatographic analysis showed that 2.3 g. of acrylamide and a small amount of propionitrile were obtained as the products. Substantially no by-products were found besides the products.

EXAMPLE 11

In the procedure described in Example 1, 8.7 g. of Raney copper which had been developed and washed with water, 18.9 g. of acrylonitrile and 81.1 g. of water were charged into an autoclave and reacted under agitation in a nitrogen atmosphere for 130 minutes at a reaction temperature of 120° C. During the reaction, the inner pressure was changed from 3 kg./cm$^2$ to 1 kg./cm$^2$. After completion of the reaction, the results of gas chromatographic analysis showed that 25.0 g. of acrylamide were obtained as the product. No by-product was found besides the product.

EXAMPLE 12

In the procedure described in Example 1, about 10 g. of Raney cobalt (Kawaken Fine Chemical, R-ODET-60 ) which had been developed and washed with water were used as catalyst and 3.3 g. of acrylonitrile and 36.0 g. of water were refluxed under agitation in the presence of the catalyst for about 2 hours at a reaction temperature of about 70° C.

After completion of the reaction, the results of gas chromatographic analysis showed that 1.06 g. of acrylamide and a small amount of propionitrile were obtained as the products together with a very small amount of an indeterminable substance.

EXAMPLE 13

In the procedure described in Example 1, a cobalt catalyst with a carrier was employed as catalyst. In a 50 ml. 2-necked, confined flask were placed 10 g. of a reduced stabilized cobalt-diatomaceous earch catalyst (Chemetron Corp.) The catalyst was heated and hydrogen gas was introduced to effect reduction. In this case, the flow rate of hydrogen was 50 ml./min., reduction temperature was 800° C. and reduction time was 2 hours. After reduction, the catalyst was cooled to room temperature while allowing introduction of a hydrogen stream. Introduction of the hydrogen stream was then stopped and a liquid mixture of 3.3 g. of acrylonitrile and 36.0 g. of water was poured onto the catalyst in such manner that the catalyst was not brought into contact with air.

The results of analysis after the reaction showed that 0.37 g. of acrylamide and a small amount of propionitrile were obtained as the products together with a very small amount of an indeterminable substance.

EXAMPLE 14

In the procedure described in Example 1, a catalyst prepared by reducing 1.0 g. of 5% palladium carbon powder (Nihon Engerhalt) at 200° C. for 2 hours with hydrogen at a flow rate of 50 ml./min. was used and a liquid mixture of 6.6 g. of acrylonitrile and 36.0 g. of water was used as reaction liquid and refluxed for 5 hours at a reaction temperature of about 70° C.

After the reaction, the catalyst was filtered off and the reaction mixture was subjected to gas chromatographic analysis. The results of analysis showed that 1.36 g. of acrylamide and a very small amount of propionitrile were obtained as the products together with a very small amount of an ideterminable substance.

EXAMPLE 15

In the procedure described in Example 1, a catalyst prepared by reducing 1.0 g. of 1% platinum carbon powder (Nihon Engerhalt) at 200° C. for 2 hours with hydrogen at a flow rate of 50 ml./min. was used and a liquid mixture of 6.6 g. of acrylonitrile and 36.0 g. of water was used as reaction liquid and refluxed for 5 hours at a reaction temperature of about 70° C.

After the reaction, the catalyst was filtered off and the reaction liquid was subjected to gas chromatographic analysis. The results of analysis showed that 0.98 g. of acrylamide was obtained as the product. No by-product was found besides the product.

EXAMPLE 16

Using the procedure described in Example 1, 0.5 g. of palladium carbon as catalyst and a mixture of 3.3 g. of acrylonitrile and 36.0 of water as reaction liquid, the experiment was conducted.

After the reaction, the catalyst was filtered off and the reaction liquid was subjected to gas chromatographic analysis the results of which showed that 0.67 g. of acrylamide and a very small amount of propionitrile were obtained as the products together with a very small amount of an indeterminable substance.

EXAMPLE 17

Using the procedure described in Example 1, 0.5 g. of plantinum black as catalyst and a mixture of 3.3 g. of acrylonitrile and 36.0 g. of water as reaction liquid, the experiment was conducted.

After the reaction, the catalyst was filtered off and the reaction liquid was subjected to gas chromatographic analysis, the results of which showed that 0.52 g. of acrylamide was obtained as the product. No by-product was found besides the product.

EXAMPLE 18

10 grams of a silver oxide catalyst on alumina carrier (1% $Ag_2O$; Toyo CCI) were placed in a 100 ml. 4-necked flask and reduced at 200° C. for 2 hours with hydrogen at a flow rate of 50 ml./min. to prepare a catalyst. Into the flask containing said catalyst was poured a mixture of 6.6 g. of acrylonitrile and 36.0 g. of water and the whole was refluxed for 2 hours at a reaction temperature of about 70° C.

After the reaction, the catalyst was filtered off and the filtrate was evaporated to yield 0.85 g. of a white crystalline product. The product was dissolved into a mixture of diethyl ether and ethanol and recrystallized therefrom to obtain a white crystalline product having a melting point of 84.5°–85° C. This product was identified as acrylamide, as the result of gas chromatographic analysis, elementary analysis, IR analysis and NMR analysis. Very small amounts of ethylene cyanohydrin and propionitrile were obtained as by-products.

EXAMPLE 19

In the procedure described in Example 18, 20 g. of the silver oxide catalyst of alumina carrier were reduced and charged into an autoclave and 13.2 g. of acrylonitrile and 72 g. of water were then charged thereinto and reacted for 2 hours at a reaction temperature of 150° C. under agitation in a hydrogen atmosphere.

After completion of the reaction, the results of gas chromatographic analysis showed that 5.85 g. of acrylamide and 2.86 g. of ethylene cyanohydrin were obtained as the products together with a very small amount of an indeterminable substance.

EXAMPLE 20

Using the procedure described in Example 18 10 g. of a silver catalyst on alumina carrier (3.5–4.0% Ag; Harshaw Chemical Co., U.S.A.) as catalyst, the reduction and reaction were carried out.

After completion of the reaction, the results of gas chromatographic analysis showed that 0.57 g. of acrylamide and 0.27 g. of ethylene cyanohydrin were obtained as the products.

EXAMPLE 21

Except that 1.0 g. of silver powder was used as catalyst in the procedure described in Example 22, the reduction and reaction were carried out.

After the reaction, the result of gas chromatographic analysis showed that 0.12 g. of acrylamide was obtained as the product together with a very samll amount of an indeterminable substance.

EXAMPLE 22

Except that 1.0 g. of gold oxide $Au_2O$ was used as catalyst in the procedure described in Example 18, the reduction and reaction were carried out.

After the reaction, the results of gas chromatographic analysis showed that 3.5 g. of acrylamide were obtained as the product together with a very samll amount of an indeterminable substance.

EXAMPLE 23

Using 1.0 g. of gold powder as catalyst in the procedure described in Example 18, the reduction was carried out and then the reaction was carried out at about 60° C. for 5 hours.

After the reaction, the results of gas chromatographic analysis showed that 0.52 g. of acrylamide and 0.13 g. of ethylene cyanohydrin were obtained as the products.

EXAMPLE 24

Using as catalyst in the procedure described in Example 1 about 10 g. of Raney copper (Kawaken Fine Chemical, CDT-60), 30.0 g. of methacrylonitrile and 13.3 g. of isopropanol were charged and reacted for 2 hours at a reaction temperature of about 70° C. under agitation at atomspheric pressure.

After the reaction, the catalyst was filtered off and the filtrate was evaporated to yield about 0.8 g. of a white crystalline product. The product was dissolved into a mixture of diethyl ether and ethanol and recrystallized therefrom to obtain a white crystalline product having a melting point of 109°-110° C. This product was identified as methacrylamide, as the result of gas chromatographic analysis, elementary analysis, IR analysis and NMR analysis. Very small amounts of acetone and an indeterminable substance were obtained as by-products.

EXAMPLE 25

In the procedure described in Example 24, 10 g. of Raney copper which had been developed and washed with water were further washed with ethanol and the composition of the reaction liquid was 30.0 g. of methacrylonitrile and 10.0 g. of ethanol. The liquid was reacted for 2 hours at a reaction temperature of about 70° C.

After the reaction, the results of gas chromatographic analysis showed that 0.6 g. of methacrylamide was obtained as the product. A small amount of an indeterminable substance was obtained as by-product.

EXAMPLE 26

In the procedure described in Example 24, about 2 g. of Raney copper which had been developed and washed with water were subjected together with a liquid mixture of 4.2 g. of methacrylonitrile and 36.0 g. of water to reaction for 2 hours at a reaction temperature of about 80° C.

After the reaction, the results of gas chromatographic analysis showed that 4.1 g. of methacrylamide were obtained as the product. No by-product was found besides the product.

EXAMPLE 27

In the procedure described in Example 24, about 2 g. of Raney copper which had been developed and washed with water were used and a reaction liquid composed of 16.8 g. of methacrylonitrile, 18.0 g. of water and 25.0 g. of dimethylformamide was reacted for 2 hours at a reaction temperature of about 80° C.

After the reaction, the results of gas chromatographic analysis showed that 12.7 g. of methacrylamide were obtained as the product. No by-product was found besides the product.

EXAMPLE 28

In the procedure described in Example 24, about 2 g. of Raney copper which had been developed and washed with water were used and a reaction liquid composed of 16.8 g. of methacrylonitrile, 18.0 g. of water and 25.0 g. of isopropanol was reacted for 2 hours at a reaction temperature of about 70° C.

After the reaction, the results of gas chromatographic analysis showed that 13.6 g. of methacrylamide were obtained as the product. No by-product was found besides the product.

EXAMPLE 29

In the precedure described in Example 24, about 2 g. of Ullmann copper which had been prepared by treating an aqueous solution of cupric nitrate with metallic zinc were used as catalyst and a liquid mixture of 4.2 g. of methacrylonitrile and 36.0 g. of water was used as reaction liquid and reacted for 2 hours at a reaction temperature of about 80° C.

After the reaction, the results of gas chromatographic analysis showed that 2.8 g. of methacrylamide were obtained as the product. Substantially no by-products were found besides the product.

EXAMPLE 30

In the procedure described in Example 24, a reduced copper catalyst was used as catalyst. 125 grams of cupric nitrate $Cu(NO_3)_2 \cdot 3H_2O$ were dissolved into 1500 ml. of water and the solution was warmed to 80° C. A 20% aqueous solution of caustic potash was added dropwise to the above solution until the pH became 9–10 to obtain cupric hydroxide. The resultant cupric hydroxide was washed well with warm water until the wash solution became neutral and then dried at 100° C. 10 grams of the resulting cupric hydroxide were charged into a 100 ml. 4-necked flask and reduced for 2 hours at 170° C. with hydrogen at a flow rate of 300 ml./min. to prepare said catalyst. Into the flask containing said reduced copper catalyst was poured a mixture of 4.2 g. of methacrylonitrile and 36.0 g. of water and the mixture was reacted for 2 hours at a reaction temperature of about 80° C.

After the reaction, the results of gas chromatographic analysis showed that 2.9 g. of methacrylamide were obtained as the product. Substantially no by-products were found besides the product.

EXAMPLE 31

In the procedure described in Example 24, a copper asbestos catalyst was used as catalyst. 15 cubic centimeters of an aqueous solution of cupric nitrate (4.2 g. as copper) were absorbed on 3 g. of asbestos which had been boiled with nitric acid, washed with water and then dried. The asbestos thus treated was added in portions to 50 cc of a boiling aqueous solution of caustic soda, filtered, washed with water and then dried. The asbestos was then charged into a 100 ml. 4-necked flask and reduced for 2 hours at 260° C. with hydrogen at a flow rate of 50 ml./min. to prepare said copper asbestos catalyst. Into the flask containing this copper asbestos catalyst was poured a liquid mixture of 4.2 g. of methacrylonitrile and 36.0 g. of water and the mixture was reacted for 2 hours at a reaction temperature of about 80° C.

After the reaction, the results of gas chromatographic anaylsis showed that 1.7 g. of methacrylamide were obtained as the product. Substantially no by-products were found besides the product.

EXAMPLE 32

In the procedure described in Example 24, copper-chromium catalyst was used as catalyst. 10 grams of copper-chromium oxide powders containing a small amount of manganese oxide (Nikki Kagaku, Copper-chromium catalyst N203) were charged into a 100 ml. 4-necked flask, reduced for 5 hours at 200° C. with hydrogen at a flow rate of 150 ml./min. and then cooled to room temperature while allowing introduction of a hydrogen stream. Into the flask containing the reduced copper-chromium was poured a liquid mixture of 4.2 g. of methacrylonitrile and 36.0 g. of water and the mixture was reacted for 2 hours at a reaction temperature of about 80° C.

After the reaction, the results of gas chromatographic analysis showed that 2.4 g. of methacrylamide were obtained as the product. Substantially no by-products were found.

EXAMPLE 33

In the procedure described in Example 24, a copper-zinc catalyst was used as catalyst. 10 grams of a cylindrically shaped material comprising copper oxide and zinc oxide (Nikki Kagaku, Copper-zinc catlyst N211) were crushed to a powder, charged into a 100 ml. 4-necked flask, reduced for 2 hours at 300° C. with hydrogen at a flow rate of 100 ml./min. and then cooled to room temperature while allowing introduction of a hydrogen stream. Into the flask containing the copper-zinc catalyst was poured a liquid mixture of 4.2 g. of methacrylonitrile and 36.0 g. of water and the mixture was reacted for 2 hours at a reaction temperature of about 80° C.

After the reaction, the results of gas chromatographic analysis showed that 1.4 g. of methacrylamide were obtained as the product. Substantially no by-products were found.

EXAMPLE 34

In the procedure described in Example 24, about 10 g. of Raney cobalt (Kawaken Fine Chemical, R-ODHT-60) which had been developed and washed with water were used as catalyst and a liquid mixture of 4.2 g. of methacrylonitrile and 36.0 g. of water was used as reaction liquid and reacted for 2 hours at a reaction temperature of about 80° C.

After the reaction, the results of gas chromatographic analysis showed that 0.9 g. of methacrylamide was obtained as the product together with a small amount of an indeterminable substance.

EXAMPLE 35

In the procedure described in Example 24, a cobalt catalyst with a carrier was used as catalyst. 10 grams of a reduction-stabilized cobalt-diatomaceous earth catalyst (Chemetron Corp.) were placed in a 50 ml. 2-necked, confined flask, heated and then reduced by passing hydrogen gas therethrough. In this case, the flow rate of hydrogen, reduction temperature and reaction time were 50 ml./min., 300° C. and 2 hours, respectively. After completion of the reduction, the catalyst was cooled to room temperature while allowing introduction of a hydrogen stream. Introduction of the hydrogen stream was then stopped and a liquid mixture of 4.2 g. of methacrylonitrile and 36.0 g. of water was poured onto the catalyst in such manner that the catalyst was not brought into contact with air. The experiment was then conducted similarly to that of Example 1.

After the reaction, the results of analysis showed that 0.8 g. of methacrylamide was obtained as the product together with a small amount of an indeterminable substance.

EXAMPLE 36

In the procedure described in Example 24, a catalyst prepared by reducing 1.0 g. of 5% palladium carbon powder (Nihon Engerhalt) at 200° C. for 2 hours with hydrogen at a flow rate of 50 ml./min. was used and a liquid mixture of 4.2 g. of methacrylonitrile and 36.0 g. of water was used as reaction liquid and reacted for 5 hours at a reaction temperature of about 80° C.

After the reaction, the catalyst was filtered off and the reaction liquid was subjected to gas chromatographic analysis, the results of which showed that 1.1 g. of methacrylamide were obtained as the product together with a very small amount of an indeterminable substance.

EXAMPLE 37

In the procedure described in Example 24, a catalyst prepared by reducing 1.0 g. of 1% platinum carbon powder (Nihon Engerhalt) at 200° C. for 2 hours with hydrogen at a flow rate of 50 ml./min. was used as catalyst and a liquid mixture of 4.2 g. of methacrylonitrile and 36.0 g. of water was used as reaction liquid and reacted for 5 hours at a reaction temperature of about 80° C.

After the reaction, the catalyst was filtered off and the reaction liquid was subjected to gas chromatographic analysis, the results of which showed that 0.8 g. of methacrylamide was obtained as the product. No by-product was found besides said product.

EXAMPLE 38

In the procedure described in Example 24, 0.5 g. of palladium black was used as catalyst and a liquid mixture of 4.2 g. of methacrylonitrile and 36.0 g. of water was used as reaction liquid and reacted for 5 hours at a reaction temperature of about 80° C.

After the reaction, the catalyst was filtered off and the reaction liquid was subjected to gas chromatographic analysis, the results of which showed that 1.2 g. of methacrylamide were obtained as the product together with a very small amount of an indeterminable substance.

EXAMPLE 39

In the procedure described in Example 24, 0.5 g. of platinum black was used as catalyst and a liquid mixture of 4.2 g. of methacrylonitrile and 36.0 g. of water was used as reaction liquid and reacted for 5 hours at a reaction temperature of about 80° C.

After the reaction, the catalyst was filtered off and the reaction liquid was subjected to gas chromatographic analysis, the results of which showed that 1.0 g. of methacrylamide was obtained as the product. No by-product was found besides said product.

EXAMPLE 40

In the procedure described in Example 24, 10 g. of a silver oxide on alumina carrier (1% $Ag_2O$; Toyo CCI) were reduced for 2 hours at 200° C. with hydrogen at a flow rate of 50 ml./min. to prepare a catalyst and a liquid mixture of 4.2 g. of methacrylonitrile and 36.0 g.

of water was subjected together with the catalyst to reaction for about 2 hours at a reaction temperature of about 80° C.

After the reaction, the results of gas chromatographic analysis showed that 1.3 g. of methacrylamide were obtained as the product. No by-product was found besides said product.

EXAMPLE 41

In the procedure described in Example 24, a catalyst prepared by reducing 1.0 g. of gold oxide $Au_2O$ at 200° C. for 2 hours with hydrogen at a flow rate of 50 ml./min. was subjected together with a liquid mixture of 4.2 g. of methacrylonitrile and 36.0 g. of water to reaction for 2 hours at about 80° C.

After the reaction, the results of gas chromatographic analysis showed that 2.1 g. of methacrylamide were obtained as the product. No by-product was found besides said product.

What is claimed is:

1. A process for the production of an amide, which comprises reacting a nitrile selected from the group consisting of acrylonitrile and methacrylonitrile with water in the presence of a catalyst consisting essentially of Raney copper.

2. A process according to claim 1 wherein the reaction is carried out at a temperature within the range of 25°–200° C. and under pressure within the range of 0–300 kg./cm².

3. A process according to claim 1 wherein the amount of water used is 0.01–100 mols per mol of said nitrile.

4. A process according to claim 1 wherein the amount of said catalyst used is 0.01–100 g. per mol of said nitrile.

5. A process according to claim 1 wherein the reaction is carried out in a suspended state.